United States Patent
Bond et al.

(10) Patent No.: US 6,167,759 B1
(45) Date of Patent: Jan. 2, 2001

(54) ULTRASONIC SYSTEM FOR GRADING MEAT

(75) Inventors: Leonard John Bond, Richland, WA (US); Doron Kishoni, Aurora; Kenneth David Mahrer, Arvada, both of CO (US)

(73) Assignee: Colorado Seminary, Denver, CO (US)

( * ) Notice: Under 35 U.S.C. 154(b), the term of this patent shall be extended for 0 days.

(21) Appl. No.: 09/499,927

(22) Filed: Feb. 8, 2000

Related U.S. Application Data

(63) Continuation of application No. 09/192,023, filed on Nov. 13, 1998, now abandoned.
(60) Provisional application No. 60/065,820, filed on Nov. 14, 1997.

(51) Int. Cl.[7] .......................................... A61B 8/00
(52) U.S. Cl. ........................... 73/602; 600/437; 600/439; 600/449
(58) Field of Search .............................. 73/597, 598, 599, 73/600, 602; 600/437, 439, 442, 443, 445, 449, 453, 459

(56) References Cited

U.S. PATENT DOCUMENTS

| | | |
|---|---|---|
| 4,030,343 | 6/1977 | Lund et al. . |
| 4,099,420 | 7/1978 | Stouffer et al. . |
| 4,409,838 | 10/1983 | Schomberg . |
| 4,512,195 | 4/1985 | Miwa et al. . |
| 4,564,019 | 1/1986 | Miwa . |
| 4,655,228 | 4/1987 | Shimura et al. . |
| 4,785,817 | 11/1988 | Stouffer . |
| 4,830,015 | 5/1989 | Okazaki . |
| 4,941,474 | 7/1990 | Pratt, Jr. . |
| 5,048,340 | 9/1991 | Thompson et al. . |
| 5,079,951 | 1/1992 | Raymond et al. . |
| 5,303,708 | 4/1994 | Stouffer . |
| 5,316,003 | 5/1994 | Stouffer . |
| 5,339,815 | 8/1994 | Liu et al. . |
| 5,353,796 | 10/1994 | Schroeder et al. . |
| 5,398,290 | 3/1995 | Brethour . |
| 5,625,147 | 4/1997 | Miles et al. . |
| 5,685,307 | 11/1997 | Holland et al. . |

FOREIGN PATENT DOCUMENTS

| | | |
|---|---|---|
| 0 337 661 A1 | 10/1989 | (EP) . |
| 0 523 865 A1 | 1/1993 | (EP) . |
| 0 523 865 B1 | 1/1993 | (EP) . |
| 2 289 763 | 11/1996 | (GB) . |
| WO 94/10562 | 5/1994 | (WO) . |
| WO 94/25857 | 11/1994 | (WO) . |
| WO 94/25867 | 11/1994 | (WO) . |
| WO 97/27755 | 8/1997 | (WO) . |

*Primary Examiner*—Hezron Williams
*Assistant Examiner*—Rose M. Miller
(74) *Attorney, Agent, or Firm*—Dorr, Carson, Sloan & Birney, P.C.

(57) ABSTRACT

An ultrasonic system for grading meat transmits an ultrasonic signal into the meat and detects the resulting back-scattered signal. The envelope of the back-scattered signal is determined. A decaying exponential curve having the form $y=\exp(-Dt)$ is fitted to the envelope, where D is the attenuation factor for the curve and t is time. A grade of the meat is then determined as a function of the attenuation factor. It may be possible to improve the accuracy of this approach by measuring the total back-scattered energy from the back-signal and generating a grade for the meat based on a polynomial function of both the attenuation factor and the total back-scattered energy. Optionally, accuracy may be further enhanced by removing any anomalies in the back-scattered signal resulting from fat deposits in the meat before calculating the attenuation factor.

8 Claims, 6 Drawing Sheets

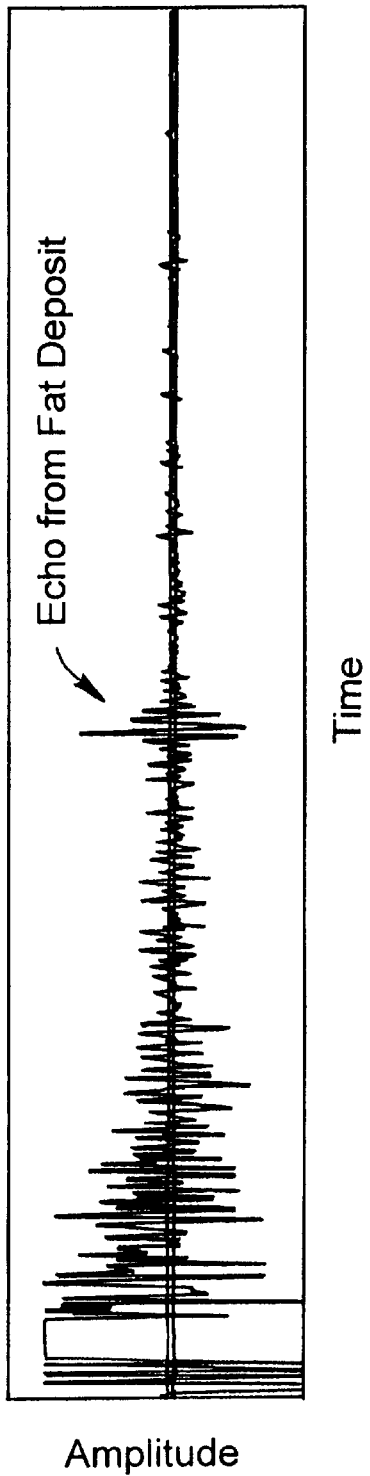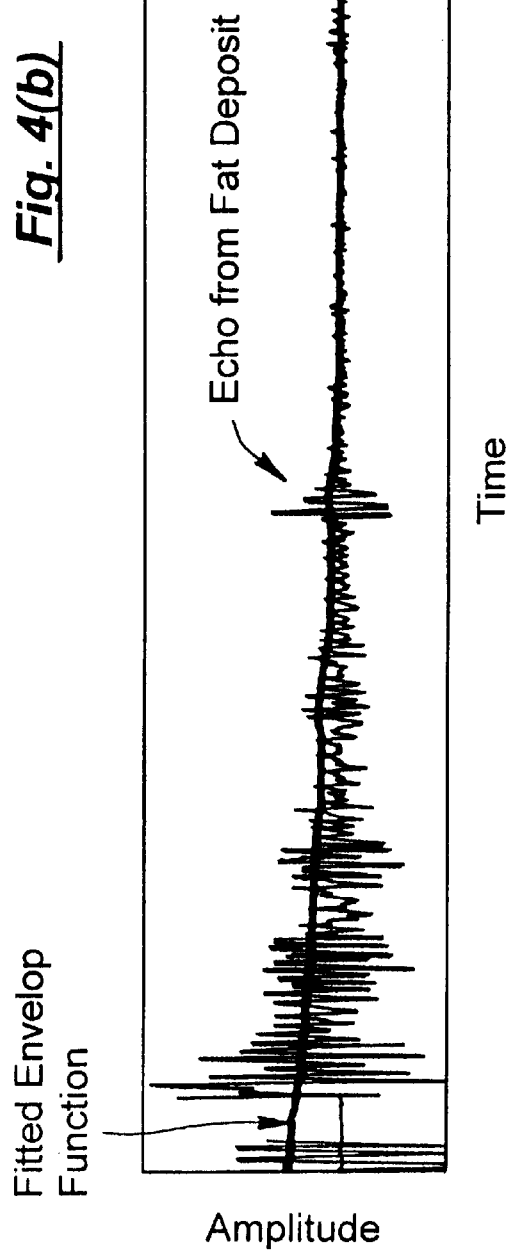

ULTRASONIC SYSTEM FOR GRADING MEAT

RELATED APPLICATION

This application is a continuation of U.S. patent application Ser. No. 09/192,023 filed on Nov. 13, 1998, now abandoned, entitled ULTRASONIC SYSTEM FOR GRADING MEAT, which in turn is based on the Applicants' U.S. Provisional patent application Ser. No. 60/065,820, entitled ULTRASONIC SYSTEM FOR GRADING MEAT, filed on Nov. 14, 1997.

BACKGROUND OF THE INVENTION

1. Field of the Invention

The present invention relates generally to the field of ultrasonics. More specifically, the present invention discloses an ultrasonic system for grading meat.

2. Statement of the Problem

Objective measures of carcass and meat quality have been major objectives within the meat and livestock industry for many years. For example, current techniques implemented by the USDA to grade beef are based on assessment of "marbling", the quantity and pattern of fat in the cut of meat. Such a grading system fails to accurately predict tenderness. In addition, the current USDA grading scheme seeks to correlate a high fat content with tenderness, which for a consumer viewpoint may discourage beef consumption. A cut of meat with a good tenderness rating and a moderate or even low fat content can provide the consumer with an attractive product.

Steaks that have low fat content and good (i.e., low) shear/tenderness values are known to exist, but cannot be identified non-destructively. They are only found after cooking and when graded by a taste panel. In contrast, the present technology is intended to perform non-destructive evaluation on live, fresh, or raw meat to identify those cuts of meat on a carcass, primal, cut meat, or a live animal that will be tender when cooked.

Various ultrasound-based technologies and other technologies have been investigated in the past for grading meat. The prior art in this field has used a range of parameters to grade meat, carcasses, or live animals, including:

(1) fat thickness (A-scan)

(2) rib-eye area, or other dimensional measurements (A and B-scan)

(3) marbling grade or percent fat (4) subjective measurements of tenderness, palatability, or eating quality based on human taste panel assessments.

The ultrasonic propagation properties of meat, including attenuation, absorption, wave speed, and the non-linearity property, are largely associated with the molecular constituents and to a lesser degree, the high-level tissue structure. However, the tenderness of meat appears to be related primarily to the higher level structure—muscle fibers and fiber bundles, myofilaments, myofribil fasciculus, combined with connective tissue. When ultrasound waves scatter from the tissue structures, rather than propagate through, the backscattered signals appear to be due primarily to the various types and the hierarchy of the higher level structure. For example, reflections from muscle boundaries can be used to determine the edges of the rib-eye. Fat structures cause the speckle in B-scan ultrasound images that can be used for marbling evaluation. Using A-scan ultrasound measurements, the weak scattering from muscle fibers, groups of fibers, and connective tissue contribute to the back-scattered signals. These back-scattered signals can be analyzed to provide an indication of tenderness in subsequently cooked meat.

The prior art includes efforts to correlate ultrasound measurements with subjective properties of meat, such as tenderness, juiciness, palatability, and flavor intensity, as determined by human taste panels on subsequently cooked samples. However, "tenderness" is also subject to objective determination by measuring the shear force necessary to cut a meat sample. In particular, Warner-Bratzler shear (W-B shear or WBS) force values have long been used as the industry standard for an objective tenderness scale. It should be expressly understood that "tenderness" is used in this objective sense in this invention. In the present invention, ultrasound is used to grade tenderness for live, fresh, or raw meat and this is calibrated against the W-B shear values obtained for the subsequently cooked sample.

Although the ultrasound-based technologies disclosed in the prior art have been implemented at some farms and packing plants, there continues to be a long-existing, unmet need in the industry for an automated system to grade carcass and meat quality.

3. Solution to the Problem

The present system uses a novel combination of ultrasonic instrumentation and signal processing algorithms to analyze the back-scattered response signals and the total energy of the back-scattered signals from a meat sample in response to ultrasonic pulses. Experimental tests have demonstrated that this methodology produces an indicator that correlates well with local Warner-Bratzler shear force values for a wide variety of subsequently cooked meat samples.

SUMMARY OF THE INVENTION

This invention provides an ultrasonic system for grading meat by analyzing the integrated back-scattered signal. An ultrasonic transducer is placed in contact with the meat sample and a series of pulses are transmitted into the sample. The transducer receives the resulting back-scattered signals from the sample and produces an output voltage corresponding to the amplitude-time (depth) response of the back-scattered signals for the measurement volume which corresponds to the transducer beam-volume. The output voltage from the transducer is amplified and digitized (preferably to a resolution of at least 12 bits per sample) by an analog-to-digital converter. In some cases, various forms of signal conditioning or filtering are employed to improve signal characteristics. This data is then analyzed or stored for later processing. Gates are implemented in software executed by a computer processor to window and sample the data. A Hilbert Transform algorithm is used to determine the envelope function of the data. The envelope generally has the shape of a decaying exponential, i.e., $y=\exp(-Dt)$, where D is the log-decrement or attenuation factor for the back-scattered signal and t is time. The log-decrement/attenuation factor has been found to correlate with the local Warner-Bratzler shear for the meat sample. The attenuation factor can be determined by fitting an exponential curve to the envelope, or by converting the envelope function to a logarithmic scale and determining the slope of the resulting line. Additional features in the time-domain, rectified data and spectral domain can be used to refine the meat grading process and to give a "marbling" score. In particular, it may be possible to improve the accuracy of this approach by measuring the total back-scattered energy from the back-scattered signals and generating a grade for the meat based on a function of both the attenuation factor and the total back-scattered energy. Optionally, accuracy of the attenuation factor may be further enhanced by removing any anomalies in the back-scattered signal resulting from fat deposits in the meat.

In addition, the anomalies in the back-scattered signal resulting from fat deposits in the meat can be analyzed to determine to the "marbling" score.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 4(a) is a graph showing a representative example of the back-scattered signal from a meat sample with a fat deposit.

FIG. 4(b) is a graph corresponding to FIG. 4(a) showing the envelop function of back-scattered signal from the meat sample, with a fat deposit.

DETAILED DESCRIPTION OF THE INVENTION

Figure 1:
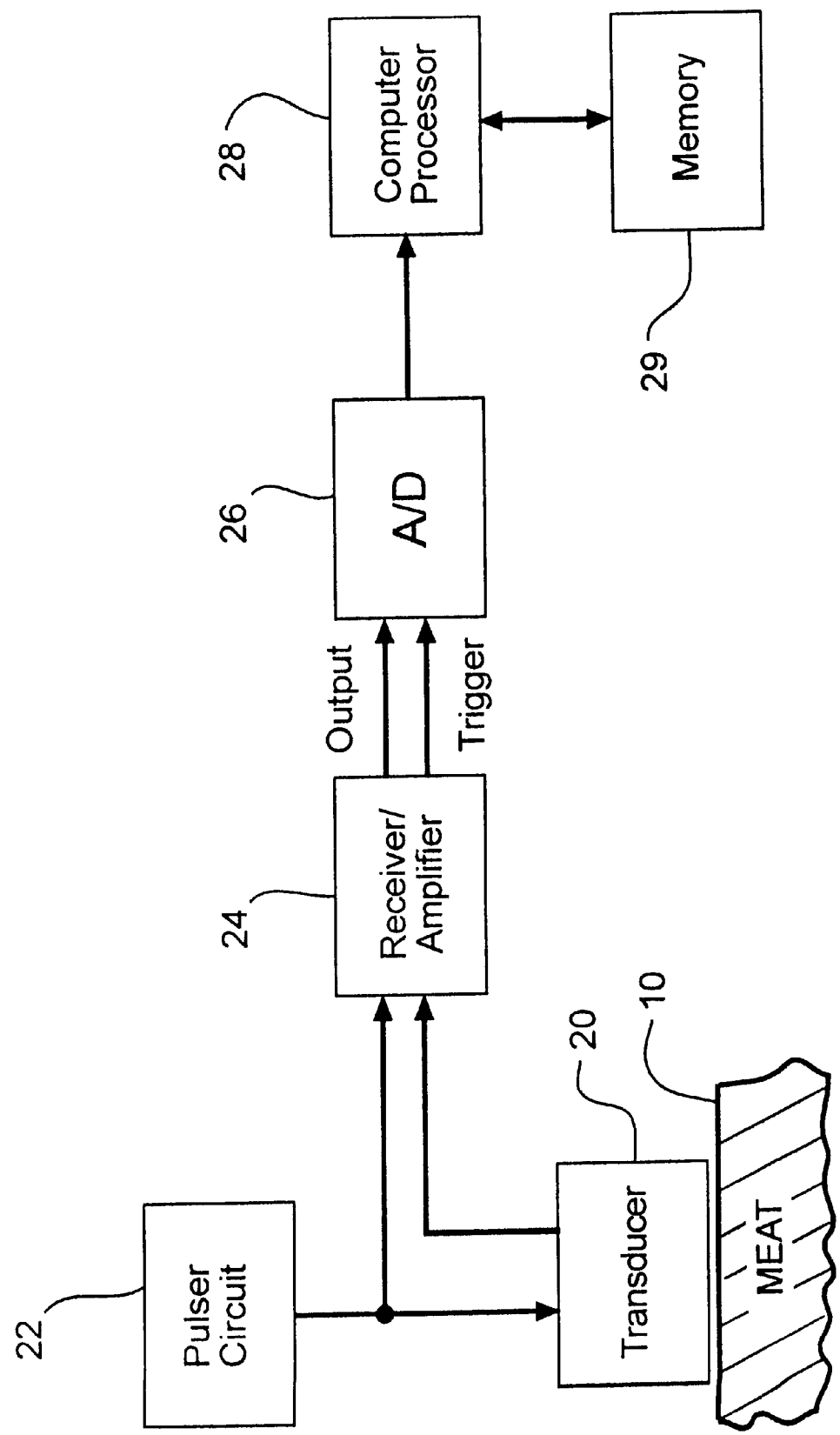
FIG. 1 is a simplified block diagram of the present system.

Turning to FIG. 1, an overview of the present system is provided. An ultrasonic transducer 20 is placed in contact with the surface of the meat sample 10. In the preferred embodiment of the present invention, the transducer 20 is placed on the edge of the meat, looking into the rib-eye, with the transducer 20 held normal to the fiber orientation. This orientation of the transducer results in the largest amplitude back-scatter signals from the muscle fibers and the most consistent gradings. A pulser circuit 22 causes the transducer to produce a series of acoustic pulses that are transmitted into the meat sample 10 (e.g., at 3.5–5 MHz).

Figure 2:
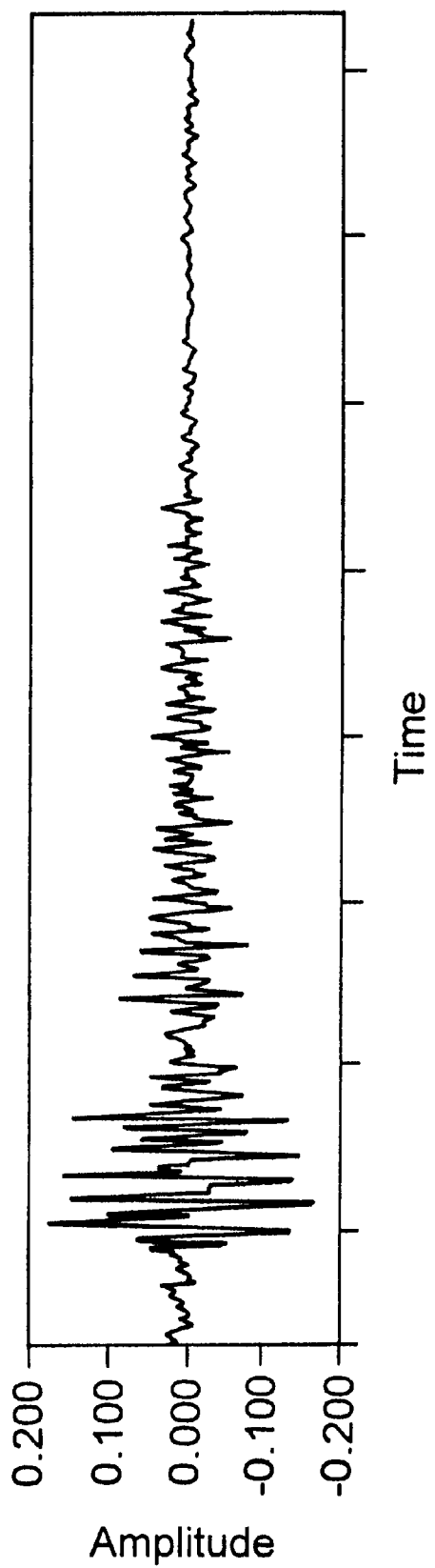
FIG. 2 is a graph showing a representative example of the back-scattered signal from a uniform meat sample with a low marbling score.

The resulting back-scattered signal from the sample 10 is detected by transducer 20, which generates an output voltage proportionate to the amplitude of the back-scattered signal as a function of depth. FIG. 2 is a graph showing an example of the back-scattered signal. A receiver/amplifier 24 amplifies the output voltage from the transducer 20 and can also be used for filtering. For example, a transducer 20, purser circuit 22, and receiver/amplifier 24 are commercially available in the Panameterics 5052 pulse-receiver unit (Panametrics Inc., Waltham, Mass., USA) or on circuit cards for integration into a PC-based instrument.

A single transducer 20 can be employed, as discussed above, or an assembly with several transducers could be placed in contact with the surface of the meat sample 10. The meat sample can be a section of tissue cut from the rib-eye area, an exposed portion of the carcass hanging in the packing plant, or an interior portion of the live animal. The ultrasonic signal from the transducer may travel though several layers of tissue or fat before reaching the tissue volume to be graded. The transducer assembly can be implemented using a collection or sparse array of transducers that could operate at different frequencies, angles of incidence to the meat, and have different beam characteristics (i.e., focal lengths). The transducer assembly can be rotated mechanically or steered electronically to maintain transducer beam orientation normal to the meat fibers. The assembly can have any of a variety of possible head configurations for each form of implementation (e.g., primal, carcass, live animal, packaged meat). Multiple transducers 20 can also be implemented using a multiplexer or multi-channel instrument.

An analog-to-digital (A/D) converter 26 periodically samples the output voltage from the receiver/amplifier 24 for each channel or transducer, and generates corresponding digital data that is transmitted to a computer processor 28. In the preferred embodiment of the present invention using a single transducer, the A/D converter 26 has a resolution of at least 12 bits and sampling rate of 60–100 MHz. A Gage A/D-digitization card (Gage Applied Sciences, South Burlington, Vt., USA) can be employed for this purpose.

Figure 3:
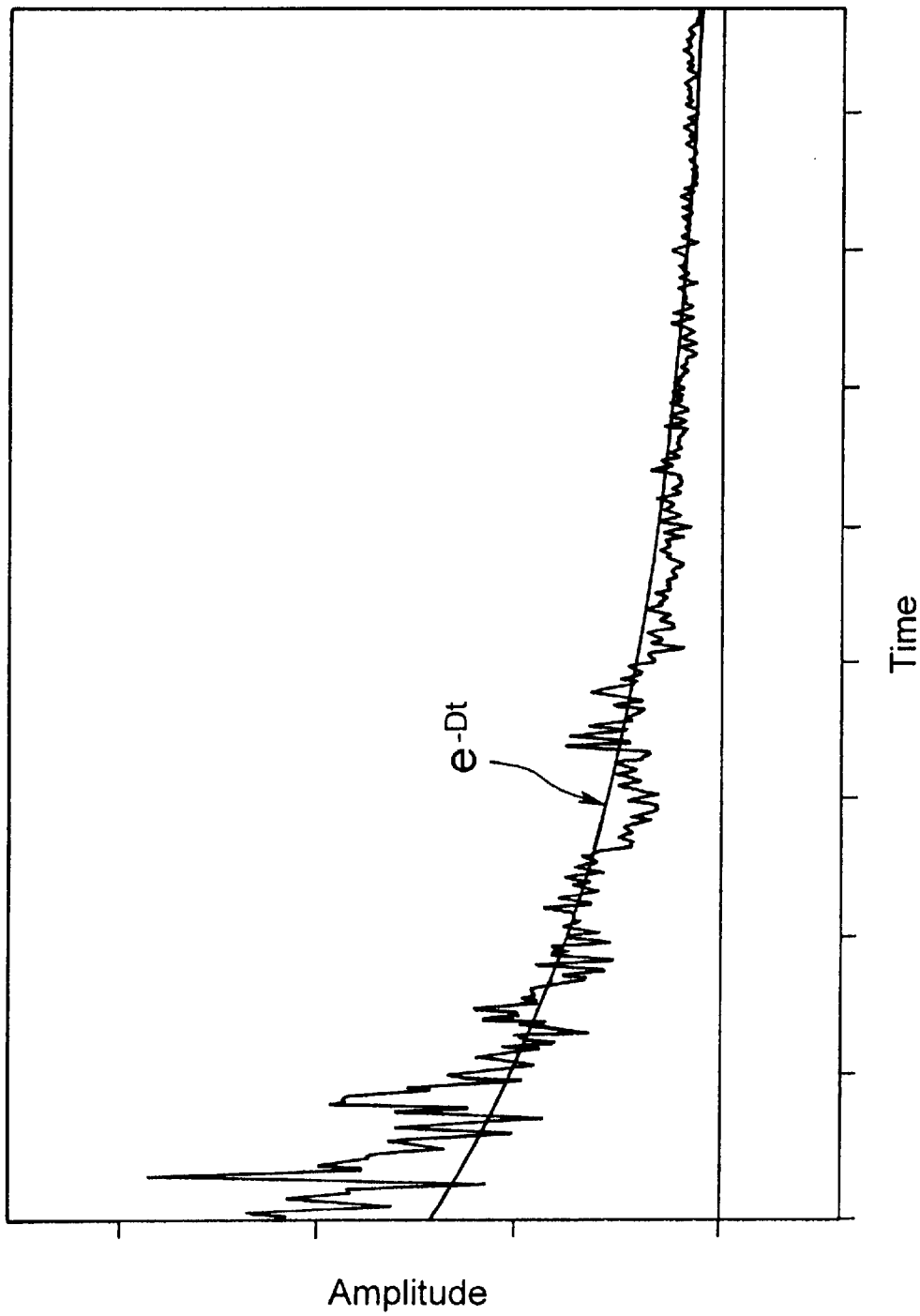
FIG. 3 is a graph showing a representative example of a rectified back-scattered signal from a meat sample of the type used to produce FIG. 2 overlaid with an exponential curve.

A processor 28 receives and stores the digitized data in memory 29 for analysis. After a series of data sets have been acquired from the back-scattered signals, the processor 28 is used for analysis of the stored data: The digitized data is retrieved from memory 29. Alternatively, the data from A/D converter 26 can be processed directly by processor 28. The processor identifies an appropriate window of data for analysis to remove artifacts of the initial pulse transmitted into the meat sample 10. The processor can use averaging or summations of multiple data traces, or the analysis of a single data trace. The data is then rectified and its envelope is determined as shown in FIG. 3. The data typically has the general shape of a decaying exponential curve, which can be approximated by $y=\exp(-Dt)$, as illustrated in FIG. 3. D is the log-decrement or attenuation factor or exponential decay factor for the curve. The attenuation factor, D, can be determined by fitting an exponential curve to the envelope, or by converting the envelope function to a logarithmic scale and determining the slope of the resulting line. For example, DADiSP software (DSP Development Corporation) or Lab-View software (National Instruments Corporation, Austin, Tex., USA) can be used for this signal processing and statistical analysis. In this manner, D values can be determined for each area of the meat sample ensonified by the transducers. An overall D value, indicative of the tenderness of the meat sample can be determined by moving the transducers to multiple locations on the sample and averaging the resulting readings.

The signal data will often contain large echo signals from fat deposits within the tissue. These deposits are more numerous and larger in more "marbled" meat samples with higher USDA grade. As shown in FIGS. 4(a) and 4(b), the echoes from fat are a signal anomaly that does not conform to the overall, exponential decay in the signal amplitude. If these echoes are included in the data used to fit the exponential decay, large in the attenuation factor can result. Various signal processing techniques can be used to compensate for the effects of fat deposits. For example, a threshold detection method can be used. In this case, the exponential fit is first calculated using all of the signal, including the fat echoes. For each portion of the signal, the signal amplitude can be compared to a threshold set to the value of the fitted exponential curve plus some fixed value. If the signal exceeds the threshold over some portion of time, then that portion is taken to be an echo from a fat deposit. To reduce the effects of fat deposits, this portion of the signal data is removed from the data used for the exponential fit calculation.

In addition, the large echoes from fat deposits in the meat sample can be analyzed to generate a separate "marbling" score for the meat. For example, time-domain or frequency-domain analysis of the back-scatter signals (including the fat echoes) can be used to provide further parameters for grading, as discussed below.

Figure 5:
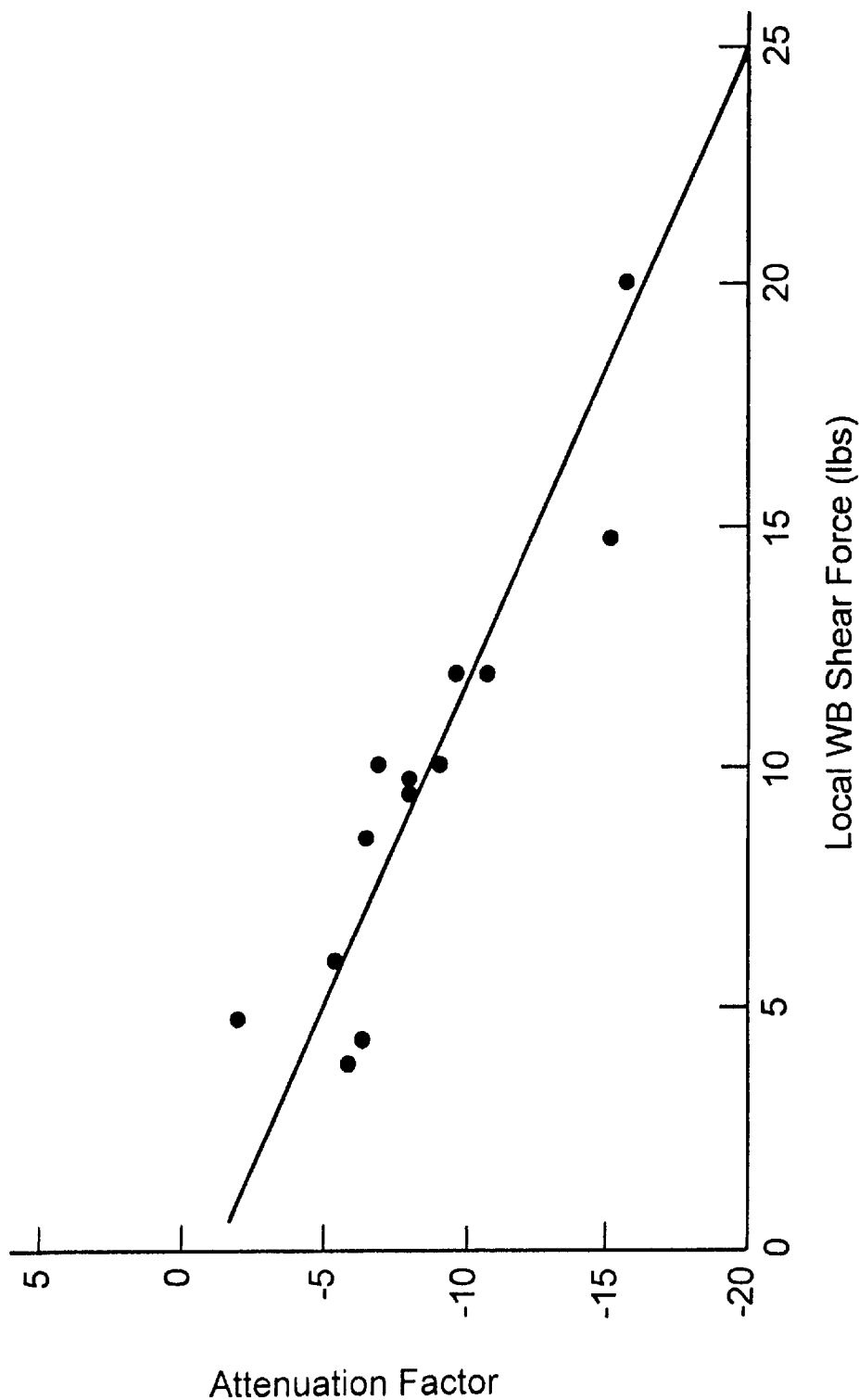
FIG. 5 is a graph showing the correlation between the attenuation factor, D, for a variety of samples and the measured local Warner-Bratzler shear force for those samples.

FIG. 5 is a graph showing the correlation between the attenuation factor, D, for a variety of low-fat meat samples 10 and the measured local Warner-Bratzler shear force. As illustrated in FIG. 5, the D value is closely correlated with the local Warner-Bratzler shear force for these meat samples 10.

Based on preliminary experimental data, it appears that it may be possible in at least some instances to enhance the accuracy of the tenderness grading by considering other factors in addition to the D value. For example, the overall amplitude of the back-scattered signals can be considered in addition to the attenuation factor, D. Tough meat typically has larger diameter, less compressible fibers than tender meat. Ultrasonic signals will be scattered from the tough fiber bundles with greater amplitude than for small, tender fiber bundles. The total back-scattered energy, S, is determined by averaging the areas under the received signal in the data analysis window.

Optionally, these parameters can be employed to form the basis for tenderness grading in meat samples, together with the attenuation factor. For example, a linear model for tenderness of the form:

$$T=a+b*D+c*S$$

can be used to calculate a numerical value for tenderness (T). The coefficients a, b, and c are determined by fitting experimental measurements of D and S to an independent measure of tenderness. For example, the independent measure may be tenderness values determined by local Warner-Bratzler shear force or through taste panel testing. After these coefficients are determined, the model can be used to convert the ultrasonic readings to a tenderness reading which varies over the same range as the independent indicators of tenderness. Other, higher-order models of D and S can be used to indicate tenderness more accurately if required.

Figure 6:
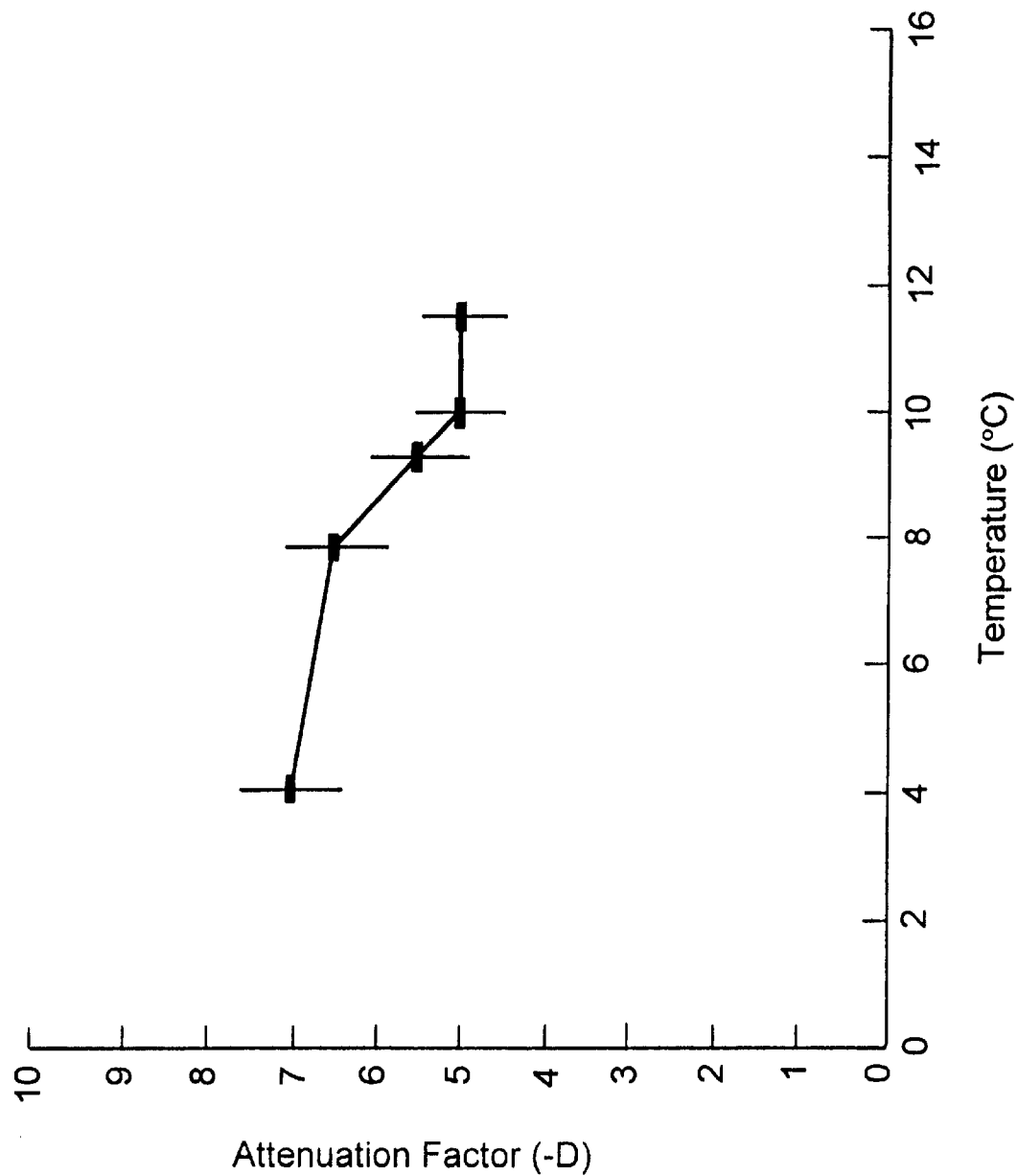
FIG. 6 is a graph showing the attenuation factor, D, for one meat sample as a function of temperature.

A systematic shift in the D value is observed as a function of sample temperature. FIG. 6 is a graph showing D value as a function of temperature for one meat sample. Corresponding temperature compensation can be incorporated into the system to produce a normalized D value.

In addition to temperature compensation, calibration is also needed to consider the history of the meat in order to accurately predict final tenderness after cooking. These factors include the species and age of the livestock, type of meat cut, aging process, storage temperature history, and tenderizing treatments that have been used with regard to the meat. This type of model permits the present invention to be used: (a) for live animals to predict final carcass quality; and (b) for carcass and primal grading to predict the tenderness after subsequent cooking.

Other time-domain or frequency-domain features of the backscattered data can be used in conjunction with the D value to increase the accuracy of grading or further refine the range of parameters used for grading. For example, frequency-domain analysis of the backscatter data may be useful in determining a "marbling" grade. B-scan images can be analyzed to generate information concerning rib-eye area, back-fat thickness, and marbling, which can be used in combination with the D value for grading meat.

The present invention can be used at any of a number of stages in the meat industry. Ranchers can use the present invention to identify live animals having desired tenderness characteristics for culling herds and breed improvement programs. Feedlot operators and ranchers can use the present invention for identifying those animals that should command a higher price, or for monitoring the effectiveness of various feeding programs. Meat packers and butchers can use the present invention as an adjunct to USDA grading to provide a means for determining the tenderness of carcasses, primals, and packaged meat. Retail stores, restaurateurs, and consumers can also use the present invention to measure the tenderness of individual cuts of meat.

As previously mentioned, conventional USDA grading is based partially on visual observation of the degree of fat marbling, which does not necessarily correlate well with the ultimate tenderness of meat. In addition, many health-conscious consumers are now seeking meat with a lower fat content, yet still has the palatability. Some cattle breeds (e.g., Texas long-horn cattle) have a lower fat content and less marbling, and therefore tend to score poorly under USDA grading. However, a significant percentage of these cattle will, in fact, produce tender low-fat meat. The present invention can be used to accurately grade such cattle and increase consumer acceptance of meat from these breeds.

We claim:

1. A method for grading meat comprising:
   transmitting an ultrasonic signal into the meat;
   detecting the resulting back-scattered signal from the meat;
   determining an envelope for said back-scattered signal as a function of time;
   fitting a decaying exponential curve to said envelope having the form $y=\exp(-Dt)$, where D is the attenuation factor for the curve and t is time; and
   determining a grade for the meat as a function of said attenuation factor.

2. The method of claim 1 wherein said grade is at least partially a function of the Warner-Bratzler shear force for the meat.

3. The method of claim 1 wherein said ultrasonic signal is transmitted into the meat in a direction substantially normal to the fibers in the meat.

4. The method of claim 1 further comprising normalizing said attenuation factor for variations in meat temperature before determining said grade.

5. An apparatus for grading meat comprising:
   an ultrasonic transducer transmitting an ultrasonic signal into the meat and generating an electrical signal in response to the resulting back-scattered signal from the meat;
   an analog-to-digital converter converting said electrical signal from said ultrasonic transducer into a time series of digital data; and
   a computer processor analyzing said digital data by:
   (a) determining an envelope for said digital data as a function of time;
   (b) fitting a decaying exponential curve to said envelope having the form $y=\exp(-Dt)$, where D is the attenuation factor for the curve and t is time; and
   (c) determining a grade for the meat as a function of said attenuation factor.

6. The apparatus of claim 5 wherein said grade is at least partially a function of the Warner-Bratzler shear force for the meat.

7. The apparatus of claim 5 wherein said ultrasonic transducer comprises a plurality of ultrasonic transducers at a plurality of locations on the meat.

8. The apparatus of claim 5 wherein said ultrasonic signal is transmitted into the meat in a direction substantially normal to the fibers in the meat.

* * * * *